(12) United States Patent
Tilbrook

(10) Patent No.: US 7,767,766 B2
(45) Date of Patent: Aug. 3, 2010

(54) METHOD OF MANUFACTURE OF POLYACROLEIN

(75) Inventor: Matthew Tilbrook, Mosman Park (AU)

(73) Assignee: Chemeq Ltd., Bentley, Western Australia (AU)

(*) Notice: Subject to any disclaimer, the term of this patent is extended or adjusted under 35 U.S.C. 154(b) by 1007 days.

(21) Appl. No.: 10/577,389

(22) PCT Filed: Nov. 5, 2004

(86) PCT No.: PCT/AU2004/001537

§ 371 (c)(1),
(2), (4) Date: Aug. 31, 2006

(87) PCT Pub. No.: WO2005/044874

PCT Pub. Date: May 19, 2005

(65) Prior Publication Data

US 2007/0083031 A1    Apr. 12, 2007

(30) Foreign Application Priority Data

Nov. 6, 2003  (AU) .............................. 2003906117

(51) Int. Cl.
  *C08F 16/00*  (2006.01)
  *C08F 8/00*   (2006.01)

(52) U.S. Cl. ................. 525/328.7; 525/326.1; 525/384; 528/230

(58) Field of Classification Search ............. 525/326.1, 525/328.7, 384; 528/230
See application file for complete search history.

(56) References Cited

U.S. PATENT DOCUMENTS

| 4,479,820 A | 10/1984 | Merk et al. |
| 4,711,892 A | 12/1987 | Manoury et al. |
| 4,724,142 A | 2/1988  | Mahn et al. |
| 4,724,143 A | 2/1988  | Mahn et al. |
| 4,847,392 A | 7/1989  | Gassman et al. |
| 5,290,894 A | 3/1994  | Melrose et al. |
| 5,917,094 A | 6/1999  | Werle et al. |
| 6,060,571 A | 5/2000  | Werle et al. |
| 6,410,040 B1 | 6/2002 | Melrose et al. |
| 6,803,356 B1 | 10/2004 | Melrose et al. |

FOREIGN PATENT DOCUMENTS

| AU | 14844/97 A    | 8/1997 |
| AU | 711548 A      | 8/1997 |
| GB | 1509154       | 4/1978 |
| WO | WO-96/38186 A | 12/1996 |
| WO | WO 00/03723   | 1/2000 |
| WO | WO-01/60874 A | 8/2001 |

*Primary Examiner*—Milton I Cano
*Assistant Examiner*—Gennadiy Mesh
(74) *Attorney, Agent, or Firm*—Nixon Peabody LLP

(57) ABSTRACT

A method of manufacture of soluble, microbiologically active and stable acrolein polymer comprising: (a) polymerising acrolein in the presence of base to form a polymer of acrolein; (b) dissolving the polymer of acrolein in an alcohol selected from monoalcohols and polyols optionally with addition of water to form an alcohol solution of the polymer of acrolein; (c) heating the alcohol solution of the polymer of acrolein; and (d) mixing base with the polymer of acrolein.

19 Claims, No Drawings

METHOD OF MANUFACTURE OF POLYACROLEIN

This application is a national stage application under 35 U.S.C. §371 from PCT Application No. PCT/AU2004/001537, filed Nov. 5, 2004, which claims the priority benefit of Australian Application No. 2003906117, filed Nov. 6, 2003.

This invention relates to a method of manufacture of polyacrolein and, in particular, to a method of manufacture of polyacrolein for use in antimicrobial compositions.

BACKGROUND

The use of polyacrolein in antimicrobial applications has been described in U.S. Pat. No. 5,290,894, Australian Application 11686/95 and its European counterpart EP 667358, in our International patent publication WO 96/38186 (PCT/AU96/00328) and more recently we have described a method of improving the activity of acrolein polymers in our International patent publication WO 01/60874 (PCT/AU00/00107).

Many of the most stable compositions of polyacrolein or use as antimicrobials are formed by heating the polymer in air. Indeed Australian Application No 11686/85 (Werle et al assigned to Degussa) teaches that only those preparations dried using the process of the invention described therein with strong air current and final air temperatures of >60° C., preferably at 75° C. are alkali soluble.

Our International Publication WO 01/60874 describes a method of improving antimicrobial activity of acrolein polymers in which the solid polymers are oxidized in air and the oxidized polymers are heated in an alcohol solution in the presence of added alkali. The presence of carboxylic acid groups formed by oxidation in air is believed to improve the solubility of polyacrolein compositions. We have now found that polyacrolein polymer of high solubility; antimicrobial activity and stability may be formed without the requirement for this aerial oxidation step.

SUMMARY

Accordingly, the present invention provides a method of manufacture of soluble, microbiologically active and stable polyacrolein comprising: (a) polymerising acrolein in the presence of base to form a polymer of acrolein; (b) dissolving the polymer of acrolein in an alcohol selected from monoalcohols and polyols, optionally with addition of water to form an alcohol solution of the polymer of acrolein; (c) heating the alcohol solution of acrolein; and (d) mixing aqueous base with the polymer of acrolein.

It is preferred that the aqueous base is mixed with the alcohol solution of the polymer of acrolein after heating of the alcohol solution of the polymer of acrolein.

The addition of base after heating, as opposed to before heating, is preferred as the addition of base after formulation affords solutions which maintain their biocidal activity for long periods upon storage.

The alcohol solution of the polymer of acrolein is preferably heated for sufficient time so that when rendered alkaline by the addition of aqueous base it does not precipitate when further diluted by a factor of one in ten.

DETAILED DESCRIPTION

In contrast with the teaching in the prior at the present invention allows stable solutions of acrolein polymers to be formed without the requirement for grinding or heating of the solid polymer in an air stream in order to oxidize the solid. This potentially reduces the expense and time required for preparation of these highly active biocides.

The acrolein polymer is formed by polymerisation of acrolein in the presence of a base such as sodium hydroxide. Polymerisation in the presence of radical initiators may also be used in preparing acrolein polymers as described in some of the examples of U.S. Pat. No. 5,290,894 but such polymers are not generally used in the process of the present invention.

The composition is dissolved in an alcohol optionally with addition of water. Dissolution of the polymer may take place as a discrete step or may occur as part of the heating process. Generally the dissolution will occur within 15 minutes of heating a PEG solution of the polymer at 35 to 65° C.

The heating of the polymer of acrolein in the alcohol solution is preferably followed by mixing of the heated solution with aqueous base. The step of heating in the alcohol is important for achieving stability of the acrolein polymer in aqueous solutions following the mixing with aqueous base. The temperature and period of heating will depend on the polymer, the type of alcohol used and the extent and term of stability required. Generally we have found that good results are obtained if the polymer of acrolein is heated for sufficient time so the when mixed with aqueous base to provide an alkaline solution the polymer will not precipitate. Preferably the polymer will not precipitate even when further diluted by a factor of one in ten (parts by volume) with water. Having regard to this type of testing a skilled person will, without undue experimentation, be able to determine appropriate heating conditions.

Following the heating step a base is mixed with the composition preferably in the form of an aqueous base composition.

The polyacrolein used in the method of the invention is formed by polymerisation of acrolein monomer conducted in an alkaline solution and the acrolein polymer may be collected as a precipitate. It will be apparent to those skilled in the art that a co-monomer, especially a water-soluble or latently water-soluble co-monomer may be used in step (a). Typically when a co-monomer is used it will constitute less than 10% by weight of the total monomer composition. We prefer that the acrolein polymer is a homopolymer.

The precipitate may, and preferably will be dissolved in the alcohol without oxidation of the solid by heating in air or oxygen, to form poly(2-propenal, 2-propenoic acid). The acrolein polymer will generally be isolated from the polymerisation reaction and is preferably heated in the alcohol with a solution of pH of no more than 7. The precipitate formed in the preferred aspect of the invention may be dissolved in the alcohol without needing to further process it.

In the process of the invention, the acrolein homopolymer is dissolved in the alcohol. This process would generally involve heating the polyacrolein in the alcohol to a temperature in the range of from 40 to 90° C. The preferred alcohol is a polyalkylene glycol and preferably has a molecular weight in the range of from 200 to 20,000. More preferably the molecular weight is in the range of from 200 to 10000 and most preferably from 200 to 2000. The acrolein polymer is heated in the alcohol to form an acetal derivative. Typically, the alcohol solution will be heated for a period of time in the range of from fifteen minutes to five hours with the alcohol and at a temperature in the range from 50 to 90° C., more preferably from 60 to 90° C.

Generally, the polyacrolein formed in step (a) used in the process of the invention will have a low acid content typically of less than 1 mole of carboxyl groups per kg of polymer and most preferably less than 0.5 mole acid groups per kilogram of polymer. Despite the low content of carboxyl groups, we have found that when the polymer is heated in the alcohol for a sufficient time and the alkali is added, the alkaline solution resists precipitation when diluted with water, which would not have been expected for an unoxidized polymer.

The process of the invention includes a step of adding base to the composition; the base is general;y added to the alcohol solution following the heating step. The pH of the resulting solution of is preferably in the range of from 7 to 9.5 and more preferably is from 7.5 to 8.5. The preferred base for addition to the alcohol solution of polyacrolein is an alkali metal carbonate particularly sodium carbonate or potassium carbonate. Alkaline metal hydroxide such as sodium hydroxide or potassium hydroxide may also be used but are less preferred. Typically the alkali is added as an aqueous solution. Preferably the solution is cooled to room temperature before adding the base in the above step.

The concentration of polymer of acrolein used in the step comprising heating in that alcohol is generally from 0.5 to 50% by weight and more preferably from 0.5 to 40% by weight. In the case of polyalkylene glycols the polyol polymer content will depend on the molecular weight of the polyol polymer. For lower molecular weight polyol polymers the content may be as high as from 50 to 90% by weight whereas for higher molecular weight polyol polymers (eg. 1500 or more) dilute compositions of the polyol polymer (eg. 2 to 50%) may be preferred.

The acrolein polymer prepared by the method of the invention is useful in a range of applications, especially antimicrobial applications. The preferred applications include antiseptic compositions, disinfectant compositions and compositions for use in treatment of gastrointestinal disease. The compositions formed in accordance with the invention generally have a good long-term antimicrobial activity. Typically, the acrolein polymers provided by the method of manufacture described above will provide a minimum kill concentration after storage at 40° C. for no less than twenty days of less than 150 ppm against a range of bacteria, e.g. $E.\ coli$, at $10^4$-$10^9$ cfu/mL.

The composition prepared by the method of the invention is particularly suited to use in administration of animals for treatment or prophylaxis of gastrointestinal disease, particularly gastrointestinal microbial infection. The composition prepared by the method of the invention may be administered to animals via drinking water, via food or other suitable means such as tablets, syrups and the like.

The invention will now be described with reference to the following examples. It is to be understood that the examples are provided by way of illustration of the invention and that they are in no way limited to the scope of the invention.

EXAMPLES

Aqueous Solution Stability Test

We found the following test ("herein referred to as the aqueous solution stability test") to be useful in determining the temperature and period of heating for providing good long term solution stability and activity.

The heated alcohol solution of acrolein polymer was allowed to cool and mixed with dilute (0.4% w/w) aqueous sodium carbonate to provide an alkaline pH. If the resulting composition showed no sign of polymer precipitate the resulting composition was diluted with water to provide a one in ten dilution composition which was again examined for a precipitate at room temperature. After a sufficient period of heating of the acrolein polymer in the alcohol solution in accordance with step (c), preferably at a temperature in the range of from 60 to 105° C., the diluted composition was clear.

Example 1

Preparation of Polyacrolein

Water (720 mL at ambient temperature, about 20° C.) and acrolein (60 g; freshly distilled, plus optionally hydroquinone added to 0.25% w/w) were placed in an open beaker, within a fume cupboard, and very vigorously stirred, mechanically. Then, 0.2 M aqueous sodium hydroxide (21.4 mL) was added to bring the pH to 10.5-11.0. The solution immediately turned a yellow typical of the hydroquinone anion and within a minute, the colour had disappeared and the clear solution became milky. About 1 minute later, precipitation of a white, flocculent polymer began, and appeared complete within 15-30 minutes. The precipitate was filtered and washed with water.

Example 2

Polyacrolein (5.0 g) was added to hot PEG-200 (64.0 g, 65 C) and the mixture stirred until the solid dissolved (20 min). $Na_2CO_{3(aq)}$ solution) (31 g of 1.29% w/w) was then added and the mixture heated at 65 C for 10 min. The mixture was then allowed to cool and the sample made up with water to 100 g to give a solution 5% w/w in polyacrolein. The pH of the neat solution was tested with PANPEHA pH sticks and the pH of a 1.0 g sample, diluted with water to 10 g total mass, was tested using a pH probe. The minimum-kill-concentration (MKC) was tested against $E.\ coli$. The composition was found to have poor stability and actually deteriorated rapidly.

Example 3

50.1 grams of the solution from Example 2 was then heated at 90 C for 2 hours. The mixture was then allowed to cool and the sample made up with water to 50 g to give a solution 5% w/w in polyacrolein. The pH of the neat solution was tested with PANPEHA pH sticks and the pH of a 1.0 g sample, diluted with water to 10 g total mass, was tested using a pH probe. The minimum-kill-concentration (MKC) was tested against $E.\ coli$.

Example 4

Polyacrolein (5.0 g) was added to hot PEG-200 (64.0 g, 65 C) and the mixture stirred until the solid dissolved (5 min). Water (25.0 g) was then added and the mixture heated at 105 C for 2 hours. The mixture was then allowed to cool and the sample made up with water (a portion of which contained $Na_2CO_3$ (0.40 g)) to 100 g to give a solution 5% w/w in polyacrolein. The pH of the neat solution was tested with PANPEHA pH sticks and the pH of a 1.0 g sample, diluted with water to 10 g total mass, was tested using a pH probe. The minimum-kill-concentration (MKC) was tested against $E.\ coli$.

Example 5

Polyacrolein (5.0 g) was added to hot PEG-200 (64.0 g, 65 C) and the mixture stirred until the solid dissolved (10 min). Water (26.0 g) was then added and the mixture heated at 90 C for 2 hours. The mixture was then allowed to cool and the sample made up with water (a portion of which contained $Na_2CO_3$ (0.40 g)) to 100 g to give a solution 5% w/w in polyacrolein. The pH of the neat solution was tested with PANPEHA pH sticks and the pH of a 1.0 g sample, diluted with water to 10 g total mass, was tested using a pH probe. The minimum-kill-concentration (MKC) was tested against *E. coli*.

Example 6

Polyacrolein (5.0 g) was added to hot PEG-200 (64.1 g, 65 C) and the mixture stirred until the solid dissolved (5 min). Water (24.6 g) was then added and the mixture heated at 105 C for 4 hours. The mixture was then allowed to cool and the sample made up with water (a portion of which contained $Na_2CO_3$ (0.40 g)) to 100 g to give a solution 5% w/w in polyacrolein. The pH of the neat solution was tested with PANPEHA pH sticks and the pH of a 1.0 g sample, diluted with water to 10 g total mass, was tested using a pH probe. The minimum-kill-concentration (MKC) was tested against *E. coli*.

Example 7

Polyacrolein (1.0 g) was added to hot PEG-200 (12.8 g, 65 C) and the mixture stirred until the solid dissolved (5 min). Water (5.2 g) was then added and the mixture heated at 90 C for 0.5 hours then at 105 C for 2 hours. The mixture was then allowed to cool and the sample made up with water (a portion of which contained $Na_2CO_3$ (0.04 g)) to 20 g to give a solution 5% w/w in polyacrolein. The pH of the neat solution was tested with PANPEHA pH sticks and the pH of a 1.0 g sample, diluted with water to 10 g total mass, was tested using a pH probe. The minimum-kill-concentration (MKC) was tested against *E. coli*.

Example 8

Polyacrolein (5.0 g) was added to hot PEG-200 (64.0 g, 65 C) and the mixture stirred until the solid dissolved (10 min). Water (20.0 g) was then added and the mixture heated at 90 C for 2 hours. The mixture was then allowed to cool and the sample made up with water (a portion of which contained $Na_2CO_3$ (0.40 g)) to 100 g to give a solution 5% w/w in polyacrolein. The pH of the neat solution was tested with PANPEHA pH sticks and the pH of a 1.0 g sample, diluted with water to 10 g total mass, was tested using a pH probe. The minimum-kill-concentration (MKC) was tested against *E. coli*.

Example 9

Polyacrolein (5.0 g) was added to hot PEG-200 (64.0 g, 65 C) and the mixture stirred until the solid dissolved (10 min). Water (20.0 g) was then added and the mixture heated at 90 C for 2 hours. The mixture was then allowed to cool and the sample made up with water (a portion of which contained $Na_2CO_3$ (0.40 g)) to 100 g to give a solution 5% w/w in polyacrolein. The pH of the neat solution was tested with PANPEHA pH sticks and the pH of a 1.0 g sample, diluted with water to 10 g total mass, was tested using a pH probe. The minimum-kill-concentration (MKC) was tested against *E. coli*.

Example 10

Polyacrolein (1.25 g) was added to hot PEG-2000 (16.0 g) at 65 C and the mixture stirred until the solid dissolved (5min). The mixture was heated at 105 C for two hours, before 0.1 g of $Na_2CO_3$ dissolved in 7.65 g of water was added to give a solution 5% w/w polyacrolein. The pH of the neat solution was tested with PANPEHA pH sticks and the pH of a 3.0 g sample diluted with water to 30 g total mass was tested using a pH probe. The minimum-kill-concentration (MKC) was tested against *E. coli*.

Example 11

Polyacrolein (1.00 g) was added to hot PEG-200 (12.81 g) at 65 C and the mixture stirred until the solid dissolved (5min). The mixture was heated at 105 C for seven hours, before cooling to room temperature. Once at room temperature 0.081 g of $Na_2CO_3$ dissolved in 6.14 g of water was added to give a solution 5% w/w polyacrolein. 1.0 g of the sample diluted with water to 10 g total mass was tested using a pH probe. The minimum-kill-concentration (MKC) was tested against *E. coli*.

Example 12

Polyacrolein (5.003 g) was added to hot PEG-200 (63.990 g) at 65 C and 0.403 g of sodium carbonate dissolved in 30.641 g of water was added. The solution was maintained at 65 C before the temperature was increased to 90 C and held for two hours. The sample was stored for 2 weeks at 40 C before the MKC was tested against *E. coli* and determined to have a MKC of 500 ppm.

Example 13

Polyacrolein (1.0 g) was added to hot PEG-200 (12.8 g, 65 C) and the mixture stirred until the solid dissolved (5 min). Water (6.29 g) was then added and the mixture heated at 90 C for 2 hours. The mixture was then allowed to cool and the sample made up with water to 20 g to give a solution 5% w/w in polyacrolein. The pH of the neat solution was tested with PANPEHA pH sticks and the pH of a 1.0 g sample, diluted with water to 10 g total mass, was tested using a pH probe. The minimum-kill-concentration (MKC) was tested against *E. coli*.

Example 14

Polyacrolein (5.0 g) was added to hot PEG-200 (64.0 g, 65 C) and the mixture stirred until the solid dissolved (10 min). The mixture was then allowed to cool and the sample made up with water to (a portion of which contained $Na_2CO_3$ (0.04 g)) to give 100 g to give a solution 5% w/w in polyacrolein. The pH of the neat solution was tested with PANPEHA pH sticks and the pH of a 3.0 g sample diluted with water to 10 g total mass, was tested using a pH probe. The minimum-kill-concentration (MKC) was tested against *E. coli*.

Example 15

Polyacrolein (5.0 g) was added to hot PEG-200 (64.1 g, 65 C) and the mixture stirred until the solid dissolved (10 min). The mixture was heated at 90 C for 2 hours. The mixture was then allowed to cool and the sample made up with water to (a portion of which contained $Na_2CO_3$ (0.20 g)) to give 100 g to give a solution 5% w/w in polyacrolein. The pH of the neat solution was tested with PANPEHA pH sticks and the pH of a 1.0 g sample diluted with water to 10 g total mass, was tested using a pH probe. The minimum-kill-concentration (MKC) was tested against *E. coli*.

Example 16

Polyacrolein (1.0 g) was added to hot PEG-200 (12.8 g, 65 C) and the mixture stirred until the solid dissolved (5 min). Water (5.2 g) was then added and the mixture heated at 90 C for 0.5 hours then at 105 C for 2 hours. The mixture was then allowed to cool and the sample made up with water to (a portion of which contained $Na_2CO_3$ (0.040 g)) to 20 g to give a solution 5% w/w in polyacrolein. The pH of the neat solution was tested with PANPEHA pH sticks and the pH of a 1.0 g sample diluted with water to 10 g total mass, was tested using a pH probe. The minimum-kill-concentration (MKC) was tested against *E. coli*

TABLE 1

| Sample (or) | Temp of dissolution | Add water | Add $Na_2CO_{3(aq)}$ | Time & Temp of $2^{nd}$ Heating | Add $Na_2CO_{3(aq)}$ | Colour | pH of heat solution | pH of 1-in-10 dilution | MKC | PPT |
|---|---|---|---|---|---|---|---|---|---|---|
| Example 2 | 65 C. | No | (0.4%) | 10 min @ 65 C. | No | yellow/orange | 8.5 | 6.85 | 31 ppm | No but poor stability |
| Example 3 | 65 C. | No | (0.4%) | 2 h @ 90 C. | No | orange | 7.0 | 6.62 | 62 ppm | No |
| Example 4 | 65 C. | Yes | No | 2 h @ 105 C. | (0.4%) | brown | 8.0 | 7.12 | 31 ppm | No |
| Example 5 | 65 C. | Yes | No | 2 h @ 90 C. | (0.4%) | brown | 8.0 | 7.11 | 62 ppm | No |
| Example 6 | 65 C. | Yes | No | 4 h @ 105 C. | (0.4%) | brown | 8.0 | 7.23 | 62 ppm | No |
| Example 7 | 65 C. | Yes | No | 2 h @ 105 C. | (0.2%) | brown | 5.0 | 5.06 | 125 ppm | No |
| Example 8 | 65 C. | Yes | No | 2 h @ 90 C. | (0.4%) | brown | 8.0 | 7.51 | 62 ppm | No |
| Example 9 | 65 C. | Yes | No | 2 h @ 90 C. | (0.4%) | brown | 8.5 | 8.69 | 125 ppm | No |
| Example 10 | 65 C. | No | No | 2 h @ 105 C. | (0.4%) | brown | 7.5 | 7.55 | 31 ppm | No |
| Example 11 | 65 C. | No | No | 7 h @ 105 C. | (0.4%) | brown | — | 8.31 | 125 ppm | No |
| Example 12 | 65 C. | No | (0.4%) | 2 h @ 90 C. | No | — | — | — | 500 ppm | No |
| Example 13 | 65 C. | Yes | No | 2 h @ 65 C. | (0.4%) | Orange | 8.0 | 7.13 | 62 ppm | ppt |
| Example 14 | 65 C. | No | No | 2 h @ 90 C. | (0.04%) | Brown | 5.0 | 3.37 | 62 ppm | ppt |
| Example 15 | 65 C. | No | No | 2 h @ 90 C. | (0.2%) | brown | 6.0 | 5.27 | 62 ppm | ppt |
| Example 16 | 65 C. | Yes | No | 2 h @ 105 C. | (0.2%) | brown | 5.0 | 5.06 | 125 ppm | No |

TABLE 2

Stability Data for Example 5

| Sample | MKC | days at r.t. | MKC | days at 40 C. | Biocidal | days at r.t. | MKC | days at 40 C. | Biocidal | days at 40 C. |
|---|---|---|---|---|---|---|---|---|---|---|
| Example 5 | 62 ppm | 2 | 31 ppm | 17 | Pass | 31 | 62 | 52 | Pass | 59 |

The Examples show that by heating the polymer in acrolein for a sufficient time at an elevated temperature, preferably above 65 C, the stability is significantly increased.

The addition of aqueous base to provide a pH of at least 7 also provides a further significant increase in stability and/or activity is demonstrated in examples 7, 14 and 16.

The aqueous base is preferably added after heating in alcohol as demonstrated by comparison of Examples 8 and 12.

The invention claimed is:

1. A method of manufacture of a soluble, microbiologically active and stable acrolein polymer comprising the following steps in sequence: (a) polymerising acrolein in the presence of base to form a polymer of acrolein; (b) dissolving the polymer of acrolein in an alcohol selected from monoalcohols and polyols optionally with addition of water to form an alcohol solution of the polymer of acrolein, and providing a pH of no more than 7, wherein the polymer of acrolein is not subject to heating in air before dissolving in alcohol; (c) heating the alcohol solution of the polymer of acrolein of pH of no more than 7, to a temperature in the range of from 40 to 105° C., to react the polymer of acrolein with the alcohol; and (d) mixing base with the polymer of acrolein, wherein the polymer product of said method does not precipitate when further diluted by water by a factor of one in ten parts by volume.

2. A method according to claim 1, wherein the polymer of acrolein comprises a co-monomer in an amount of up to 10% by weight of the total monomer composition.

3. A method according to claim 1, wherein the polymer of acrolein is a homopolymer.

4. A method according to claim 1, wherein the polymer of acrolein is collected from the polymerisation reaction as a precipitate and dissolved in the alcohol.

5. A method according to claim 1, wherein the polymer of acrolein is isolated as a solid from the step of polymerisation in the presence of base.

6. A method according to claim 1, wherein said heating step is carried out at a temperature in the range of from 40 to 90° C.

7. A method according to claim 1, wherein alcohol is a polyalkylene glycol.

8. A method according to claim 1, wherein said heating step is carried out at a temperature in the range from 50 to 105° C., for a period in the range of from fifteen minutes to five hours.

9. A method according to claim 1, wherein the polymer of acrolein dissolved in the alcohol in step (b) has an acid content of less than 1 mole of carboxyl groups per kilogram of polymer.

10. A method according to claim 9, wherein said acid content is less than 0.5 mole carboxyl groups per kilogram of polymer.

11. A method according to claim 1, wherein the base is added to the alcohol solution following said heating step.

12. A method according to claim 11, wherein the pH of the resulting solution is in the range of from 7 to 9.5.

13. A method according to claim 11, wherein the pH of the resulting solution is in the range of from 7.5 to 8.5.

14. A method according to claim 1, wherein the base comprises a compound selected from the group consisting of alkali metal carbonate, alkali metal hydroxide, and mixtures thereof.

15. A method according to claim 14, wherein the base comprises sodium carbonate and/or potassium carbonate.

16. A method according to claim 1, wherein the polymer of acrolein used in the step of heating in the alcohol is in a concentration in the alcohol of from 0.5 to 50% by weight.

17. A method according to claim 16, wherein the concentration is from 0.5 to 40% by weight.

18. A method according to claim 1, wherein the alcohol is polyethylene glycol and is present at a concentration in the range of from 5 to 90% by weight.

19. A method according to claim 1, wherein the alcohol is a polyethylene glycol of molecular weight in the range of from 200 to 20,000.

* * * * *